(12) United States Patent
List et al.

(10) Patent No.: US 7,645,908 B2
(45) Date of Patent: Jan. 12, 2010

(54) METHOD FOR HYDROGENATION OF α, β-UNSATURATED CARBONYL COMPOUNDS

(75) Inventors: Benjamin List, Mulheim an der Ruhr (DE); Jung Woon Yang, Mulheim an der Ruhr (DE)

(73) Assignee: Studiengesellschaft Kohle mbH, Mülheim an der Ruhr (DE)

( * ) Notice: Subject to any disclaimer, the term of this patent is extended or adjusted under 35 U.S.C. 154(b) by 371 days.

(21) Appl. No.: 11/575,802

(22) PCT Filed: Sep. 27, 2005

(86) PCT No.: PCT/DE2005/001705

§ 371 (c)(1), (2), (4) Date: Mar. 22, 2007

(87) PCT Pub. No.: WO2006/034692

PCT Pub. Date: Apr. 6, 2006

(65) Prior Publication Data

US 2009/0182174 A1    Jul. 16, 2009

(30) Foreign Application Priority Data

Sep. 29, 2004   (DE) ................. 10 2004 047 794

(51) Int. Cl.
    *C07C 45/00*     (2006.01)
(52) U.S. Cl. ............... 568/312; 568/433; 568/458
(58) Field of Classification Search ............. 568/312, 568/433, 458
See application file for complete search history.

(56) References Cited

U.S. PATENT DOCUMENTS

| | | | | | |
|---|---|---|---|---|---|
| 4,260,829 | A | * | 4/1981 | Horner et al. | ............. 568/462 |
| 4,271,323 | A | * | 6/1981 | Durand et al. | ............. 568/816 |
| 4,940,819 | A | * | 7/1990 | Kiel et al. | ............. 568/318 |

OTHER PUBLICATIONS

Torchy et al; "Hydrogen transfer from hanzsch 1,4-dihydropyridines to carbon-carbon double bonds under microwave irradiation"; Molecules (2002), 7, pp. 528-533.
Inoue et al; "Selective reduction of carbon-carbon double bonds with an NAD(P)H model-acetic acid system"; Bull. Chem. Soc. Jpn.,(1988), 61, pp. 3020-3022.
Nakamura, et al; "NAD(P)+—NAD(P)II Model. 52. Reduction of olefins by hantzsfch ester on silica gel"; Tetrahedron Letters, vol. 25, No. 36, (1984), pp. 3983-3986.

\* cited by examiner

*Primary Examiner*—Sikarl A Witherspoon
(74) *Attorney, Agent, or Firm*—Norris McLaughlin & Marcus, P.A.

(57) ABSTRACT

A method for the chemoselective hydrogenation of α, β unsaturated carbonyl compounds is disclosed, in which compounds of the formula $R^4R^3C{=}CR^2{-}C(O)R^1$, wherein $R^1{-}R^4$ are as defined herein, are reacted with a hybrid donor to form a compound of formula $R^4R^3CH{-}CH(R^2){-}C(O)R^1$, in which $R^1{-}R^4$ are as above. That method permits the selective hydrogenation of α, β unsaturated aldehydes and ketones without the use of metal catalysts.

6 Claims, No Drawings

METHOD FOR HYDROGENATION OF α, β-UNSATURATED CARBONYL COMPOUNDS

This application is a 371 of PCT/DE2005/001705, filed Sep. 27, 2005, which claims foreign priority benefit under 35 U.S.C. § 119 of the German Patent Application No. 10 2004 047 794.9 filed Sep. 29, 2004.

The present invention relates to a process for hydrogenating α,β-unsaturated carbonyl compounds.

Branched carbonyls are very valuable intermediates in the synthesis of pharmaceutical compounds, odorants, natural products and other functional substances. For example, citronellal is a β-branched aldehyde which is used as an odorant and also industrially in important syntheses of citronellol, menthol, muscone and α-tocopherol. Interestingly, the citronellal obtained from natural sources is not enantiomerically pure. A process which allows its enantiomerically pure synthesis is therefore important.

Scheme 1. A beta-branched aldehyde of industrial relevance.

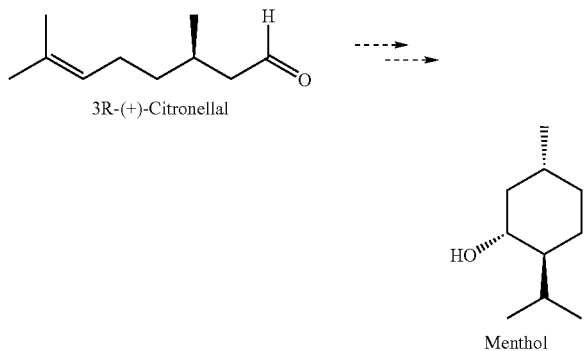

3R-(+)-Citronellal

Menthol

Possible routes to enantiomerically pure branched carbonyl compounds are catalytic asymmetric hydrogenation and conjugated reduction of the corresponding α,β-unsaturated carbonyl compounds.

Scheme 2. Hydrogenation of unsaturated α, β-carbonyl compounds.

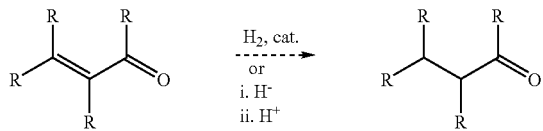

A series of examples of these two reaction types have been described in the literature, all based on metal catalysis, and catalytic asymmetric hydrogenations have to date only been employed successfully with ketones, but not with aldehydes. An additional problem is that existing processes are often not chemoselective. Often, further functional groups are also reduced as well as the double bond in this case, which is undesired. The enantioselectivity is also often unsatisfactory. Catalytic asymmetric hydrogenations of aldehydes are to date completely unknown.

A further disadvantage of metal catalysis is that the hydrogenating agent used is $H_2$ gas at pressures above atmospheric pressure. The use of gaseous reactants regularly entails a high level of apparatus complexity. An additional factor is that the noble metal-based catalysts are very expensive. The catalysts therefore not only have to be removed from the end product but also processed in order to be able to use the noble metal fractions in a further process.

It was an object of the present invention to provide a simple process for preparing branched carbonyl compounds, in which the metal catalysts can be dispensed with and the process should not be restricted to ketones but also applicable to aldehydes.

The present invention provides a process for hydrogenating α,β-unsaturated carbonyl compounds, in which a compound with the general formula I

(I)

in which $R^1$ is H, a branched or unbranched, saturated or unsaturated hydrocarbon radical which has from 1 to 30 carbon atoms and may have suitable substituents, where the hydrocarbon radical may have one or more heteroatoms in the chain, an aryl group or heteroaryl group which may have suitable substituents, $R^2$, $R^3$ and $R^4$ may be the same or different and are each H, F, Cl, Br, I, OH, CN, $NO_2$, NO, $SO_2$, $SO_3^-$, amino, mono- and di-($C_1$-$C_{24}$-alkyl)-substituted amino, mono- and di-($C_5$-$C_{20}$-aryl)-substituted amino, imino, phosphono, phosphonato, phosphinato, phospho, phosphino, a branched or unbranched, saturated or unsaturated hydrocarbon radical which has from 1 to 30 carbon atoms and may have suitable substituents, where the hydrocarbon radical may have a heteroatom in the chain, an aryl group or heteroaryl group which may have suitable substituents, where in each case 2 or more of the $R^1$, $R^2$, $R^3$ and $R^4$ radicals may form a 5- or 6-membered ring or fused 5-membered and/or 6-membered rings, which may be aromatic, alicyclic, heteroaromatic or heteroalicyclic and may have up to 4 substituents, is reacted with a hydride donor to form a compound with the general formula II

(II)

in which $R^1$, $R^2$, $R^3$ and $R^4$ are each as defined above.

By virtue of the process according to the invention, it is possible to catalytically reduce α,β-unsaturated carbonyl compounds in a highly chemoselective manner, and it is possible to dispense with the use of metal catalysts. Two variants of the process have been developed, which are suitable firstly for non-asymmetric reductions to form racemic mixtures and secondly for highly enantiolselective reductions.

One example of the process procedure is shown in scheme 3 below using the example of the reaction of an α,β-unsaturated carbonyl compound with a dihydropyridine as the hydride donor. In this scheme, an amine or an ammonium salt is used as the catalyst.

Scheme 3. Catalytic metal-free hydrogenation of α, β-unsaturated carbonyl compounds.

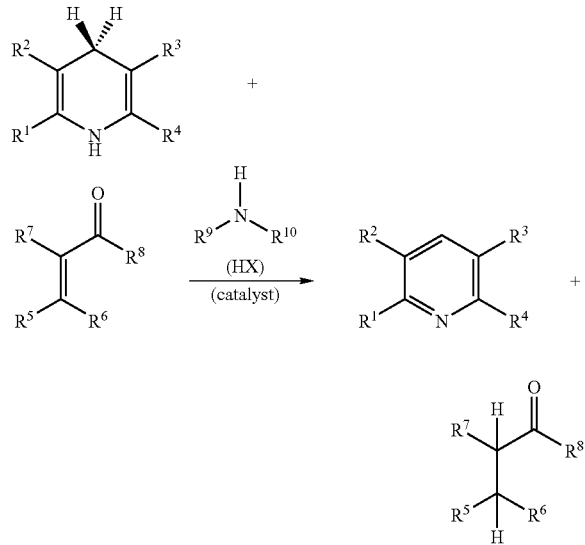

The $R^1$, $R^2$, $R^3$ and $R^4$ radicals may each be as defined above. The branched or unbranched, saturated or unsaturated hydrocarbon radical having from 1 to 30 carbon atoms is preferably selected from $C_1$-$C_{24}$-alkyl, $C_2$-$C_{24}$-alkenyl, $C_2$-$C_{24}$-alkynyl, $C_1$-$C_{24}$-alkoxy, $C_2$-$C_{24}$-alkenyloxy, $C_2$-$C_{24}$-alkynyloxy, $C_5$-$C_{30}$-aryl, $C_5$-$C_{30}$-aryloxy, $C_2$-$C_{24}$-alkoxyalkyl, $C_6$-$C_{30}$-aryloxyalkyl, hydroxyl, sulfhydryl, $C_2$-$C_{24}$-alkylcarbonyl, $C_6$-$C_{30}$-arylcarbonyl, $C_2$-$C_{24}$-alkoxycarbonyl, $C_6$-$C_{30}$-aryloxy-carbonyl, halocarbonyl, $C_2$-$C_{24}$-alkylcarbonato, $C_6$-$C_{30}$-arylcarbonato, carboxyl, carboxylato, carbamoyl, mono- and di-($C_1$-$C_{24}$-alkyl)-substituted carbamoyl, $C_2$-$C_{24}$-alkylamido, $C_6$-$C_{30}$-arylamido, $C_2$-$C_{24}$-alkylimino, $C_6$-$C_{30}$-arylimino, $C_1$-$C_{24}$alkylsulfanyl, $C_5$-$C_{30}$-arylsulfanyl, $C_1$-$C_{24}$-alkylsulfinyl, $C_5$-$C_{30}$-arylsulfinyl, $C_1$-$C_{24}$-alkylsulfonyl, $C_5$-$C_{30}$-arylsulfonyl.

The term "alkyl" used means a linear, branched or cyclic hydrocarbon radical which has typically from 1 to 30, preferably from 1 to 24 carbon atoms, such as methyl, ethyl, n-propyl, isopropyl, n-butyl, isobutyl, t-butyl, octyl, decyl, etc., but also cycloalkyl groups such as cyclopentyl, cyclohexyl, etc. The hydrocarbon radicals have preferably from 1 to 18, in particular from 1 to 12 carbon atoms.

The term "alkenyl" used means a linear, branched or cyclic hydrocarbon radical which has at least one double bond and typically has from 2 to 30, preferably from 2 to 24 carbon atoms, such as ethenyl, n-propenyl, isopropenyl, n-butenyl, isobutenyl, octenyl, decenyl, tetradecenyl, hexadecenyl, eicosenyl, tetracosenyl, etc., but also cycloalkenyl groups such as cyclopentenyl, cyclohexenyl, etc. The alkenyl radicals preferably have from 2 to 18, in particular from 2 to 12 carbon atoms.

The term "alkynyl" used means a linear, branched or cyclic hydrocarbon radical which has at least one triple bond and has typically from 2 to 30, preferably from 2 to 24 carbon atoms, such as ethynyl, n-propynyl, isopropynyl, n-butynyl, isobutynyl, octynyl, decynyl, tetradecynyl, hexadecynyl, eicosynyl, tetracosynyl, etc. The alkynyl radicals preferably have from 2 to 18, in particular from 2 to 12 carbon atoms.

Preferred alkoxy groups are methoxy, ethoxy, n-propoxy, isopropoxy, n-butyloxy, isobutyloxy, t-butyloxy, pentyloxy, hexyloxy, etc.

The aryl groups used in the context of the present invention are aromatic ring systems which have from 5 to 30 carbon atoms and optionally heteroatoms such as N, O, S, P, Si, in the ring, where the rings may be single or multiple ring systems, for example fused ring systems or rings bonded to one another via single bonds or multiple bonds. Examples of aromatic rings are phenyl, naphthyl, biphenyl, diphenyl ether, diphenylamine, benzophenone and the like. Substituted aryl groups have one or more substituents as have already been specified in the definition of $R^1$. Examples of heteroalkyl groups are alkoxyaryl, alkylsulfanyl-substituted alkyl, N-alkylated aminoalkyl and the like. Examples of heteroaryl substituents are pyrrolyl, pyrrolidinyl, pyridinyl, quinolinyl, indolyl, pyrimidinyl, imidazolyl, 1,2,4-triazolyl, tetrazolyl and the like. Examples of heteroatom-containing alicyclic groups include pyrrolidino, morpholino, piperazino, piperidino, etc.

As substituents which have the aforementioned group may be OH, F, Cl, Br, I, CN, $NO_2$, NO, $SO_2$, $SO_3^-$, amino, mono- and di-($C_1$-$C_{24}$-alkyl)-substituted amino, mono- and di-($C_5$-$C_{20}$-aryl)-substituted amino, imino, which may in turn be substituted. Especially the cyclic radicals may also have $C_1$-$C_6$-alkyl groups as substituents.

As functional groups, the above-defined radicals or the substituents may contain all groups which are known to those skilled in the art and are customary in organic synthesis, such as halogen, hydroxyl, sulfhydryl, $C_1$-$C_{24}$-alkoxy, $C_2$-$C_{24}$-alkenyloxy, $C_2$-$C_{24}$-alkynyloxy, $C_5$-$C_{20}$-aryloxy, acyl and $C_2$-$C_{24}$-alkylcarbonyl (—CO-alkyl) and $C_6$-$C_{20}$-arylcarbonyl (—CO-aryl), acyloxy (—O-acyl) $C_2$-$C_{24}$-alkoxycarbonyl (—(CO)—O-alkyl), $C_6$-$C_{20}$-aryloxycarbonyl (—(CO)—O-aryl), halocarbonyl (—(CO)—X in which X is halogen), $C_2$-$C_{24}$-alkylcarbonato (—O—(CO)—O-alkyl), $C_6$-$C_{20}$-arylcarbonato (—O—(CO)—O-aryl), carboxyl (—COOH)$_1$ carboxylato (—COO$^-$), carbamoyl (—(CO)—$NH_2$), monosubstituted $C_1$-$C_{24}$-alkylcarbamoyl (—(CO)—NH($C_1$-$C_{24}$-alkyl)), disubstituted alkylcarbamoyl (—(CO)—N($C_1$-$C_{24}$-alkyl) 2), monosubstituted arylcarbamoyl (—(CO)—NH-aryl), thiocarbamoyl (—(CS)—$NH_2$), carbamido (—NH—(CO)—$NH_2$), cyano (—C≡N), isocyano —N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—$NH_2$), mono- and di-($C_1$-$C_{24}$-alkyl)-substituted amino, mono- and di-($C_5$-$C_{20}$-aryl)-substituted amino, $C_2$-$C_{24}$-alkylamido (—NH—(CO)-alkyl), $C_5$-$C_{20}$-arylamido (—NH—(CO)-aryl), imino (—CR=NH, in which R=H, $C_1$-$C_{24}$-alkyl, $C_5$-$C_{20}$-aryl, $C_6$-$C_{20}$-alkaryl, $C_6$-$C_{20}$-aralkyl, etc.), alkylimino (—CR=N(alkyl), in which R=H, alkyl, aryl, alkaryl, etc.), arylimino (—CR=N(aryl), in which R=H, alkyl, aryl, alkaryl, etc.), nitro (—$NO_2$), nitroso (—NO), sulfo (—$SO_2$—OH), sulfonato (—$SO_2$—O$^-$), $C_1$-$C_{24}$-alkylsulfanyl (—S-alkyl; also known as "alkylthio"), arylsulfanyl (—S-aryl; also known as "arylthio"), $C_1$-$C_{24}$-alkylsulfinyl (—(SO)-alkyl), $C_5$-$C_{20}$-arylsulfinyl (—(SO)-aryl), $C_1$-$C_{24}$alkylsulfonyl (—$SO_2$-alkyl), $C_5$-$C_{20}$-arylsulfonyl (—$SO_2$-aryl), phosphono (—P(O) (OH)$_2$), phosphonato —P(O) (O$^-$)$_2$) phosphinato (—P(O)(O$^-$)), phospho (—$PO_2$) and phosphino (—PH$_2$); and the hydrocarbon radicals C$_1$-C$_{24}$-alkyl, preferably C$_1$-C$_{18}$-alkyl, more preferably C$_1$-C$_{12}$-alkyl, in particular C$_1$-C$_6$-alkyl, C$_2$-C$_{24}$-alkenyl, preferably C$_2$-C$_{18}$-alkenyl, more preferably C$_2$-C$_{12}$-alkenyl, in particular C$_2$-C$_6$-alkenyl, C$_2$-C$_{24}$-alkynyl, preferably C$_2$-C$_{18}$-alkynyl, more preferably C$_2$-C$_{12}$-alkynyl, in particular C$_2$-C$_6$-alkynyl, C$_5$-C$_{30}$-aryl, preferably C$_5$-C$_{20}$-aryl, more preferably C$_5$-C$_{12}$-aryl, and C$_6$-C$_{30}$-aralkyl, preferably C$_6$-C$_{20}$-aralkyl, more preferably C$_6$-C$_{12}$-aralkyl.

According to the invention, the compounds with the formula I are reacted with a hydride donor. Useful hydride donors include all compounds which can release hydride ions, preference being given to organic hydride donors. Suitable hydride donors are, for example, Hantzsch dihydropyridine. In a preferred embodiment of the present invention, a dihydropyridine of the general formula III is used

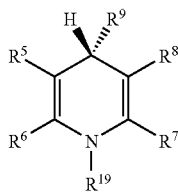

(III)

in which R$^5$, R$^6$, R$^7$, R$^8$ and R$^9$ may be the same or different and are each H, OH, a saturated or unsaturated, straight-chain, branched or cyclic, unsubstituted or substituted C$_1$-C$_{20}$-alkyl radical, halogen, especially F, Cl, Br, I, NO$_2$, an amino group, —CO$_2$R$^{10}$, C(O)R$^{11}$, C—O—R$^{12}$, OR$^{13}$, where R$^{10}$ to R$^{13}$ may each be selected from H, branched or unbranched, saturated or unsaturated hydrocarbon radicals which have 1 to 30 carbon atoms and may have suitable substituents, where the hydrocarbon radicals may have one or more heteroatoms in the chain, aryl groups or heteroaryl groups, which may in turn have suitable substituents, and R$^{19}$ is H, a branched or unbranched, saturated or unsaturated hydrocarbon radical which has from 1 to 30 carbon atoms and may contain suitable substituents, where the hydrocarbon radicals may have one or more heteroatoms in the chain and suitable substituents, aryl groups or heteroaryl groups which may in turn have suitable substituents, and salts of the compounds with the formula III.

In the compounds with the formula III, R$^5$ and R$^8$ are preferably selected from the electron-withdrawing radicals such as halogen, NO$_2$, —CO$_2$R$^{10}$, C(O)R$^{11}$, C—O—R$^{12}$, OR$^{13}$, where R$^{10}$ to R$^{13}$ may each be as defined above. R$^6$ and R$^7$ are preferably selected from H or a C$_1$-C$_6$-alkyl group, R$^9$ is preferably hydrogen or a C$_1$-C$_6$-alkyl group, and R$^{19}$ is preferably H or a C$_1$-C$_6$-alkyl group.

Examples of further hydride donors include secondary alcohols, silanes, triarylmethanes, cyclohexadienes, formaldehyde and its derivatives, formic acid and its derivatives and salts.

The selectivity and efficiency of the process according to the invention can be improved further when the reaction is performed in the presence of a catalyst. The performance of the reaction in the presence of a catalyst can be effected in different configurations. In one possible embodiment, the catalyst is selected from organic bases, especially primary and secondary amines and their acid addition salts, especially amines with the general formula IV

NHR$^{14}$R$^{15}$ (IV)

in which

R$^{14}$ is H, a hydrocarbon group such as a saturated or unsaturated, branched or linear alkyl group, alkenyl group, alkynyl group, aryl, alkylaryl, which may have suitable substituents, or a heteroatom-containing hydrocarbon group which may have suitable substituents, and R$^{15}$ is a hydrocarbon group such as a saturated or unsaturated, branched or linear alkyl group, alkenyl group, alkynyl group, aryl, alkylaryl, which may have suitable substituents, a heteroatom-containing hydrocarbon group which may have suitable substituents, where R$^{14}$ and R$^{15}$ may form a fused, substituted or unsubstituted ring which has from 3 to 7 carbon atoms and may, in addition to the nitrogen atom from formula IV, also contain a further heteroatom, and their acid addition salts.

When R$^{14}$ and R$^{15}$ together form a ring, the radicals are selected so as to obtain preferably a 5- or 6-membered alicyclic or aromatic ring, such as pyrrolidinyl, piperidinyl, morpholinyl, pyrrolyl, pyridinyl, pyrimidinyl, imidazolyl, etc.

Acids suitable for forming the acid addition salts are selected from inorganic acids, especially from HCl, H$_2$SO$_4$, H$_2$SO$_3$, HNO$_3$, HNO$_2$, HClO$_4$, H$_3$PO$_4$, chromic acid and suitable combinations thereof, and organic acids, especially carboxylic acids, sulfonic acids, phosphonic acids, phenols having from 1 to 5 electron-withdrawing substituents. Examples of suitable organic acids are acetic acid, propionic acid, glycolic acid, pyruvic acid, oxalic acid, malic acid, malonic acid, succinic acid, maleic acid, fumaric acid, tartaric acid, citric acid, benzoic acid, 2-nitrobenzoic acid, cinnamic acid, mandelic acid, methanesulfonic acid, ethanesulfonic acid, trifluorosulfonomethane acid, p-toluenesulfonic acid, salicylic acid, chloroacetic acid, dichloroacetic acid, trichloroacetic acid, trifluoroacetic acid and combinations thereof.

Compounds with the formula III which are used with preference are secondary amines, i.e. R$^{14}$ is not hydrogen. For the non-asymmetric procedure, preference is given to using non-chiral amines, for example compounds in which R$^{14}$ and R$^{15}$ are each selected from methyl, ethyl, propyl, butyl, cyclopentyl, cyclohexyl, cyclooctyl, phenyl, naphthyl, benzyl or trimethylsilyl. Further preferred amines are those in which the nitrogen atom and the R$^{14}$ and R$^{15}$ radicals form a 3- to 15-membered, optionally substituted ring. Particular preference is given to using amines having at least one chiral center in the molecule. Particularly suitable compounds have been found to be imidazolidinone and its derivatives with the general formula V:

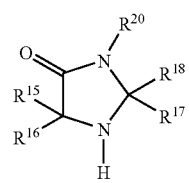

(V)

in which

R$^{15}$, R$^{16}$, R$^{17}$ and R$^{18}$ may be the same or different and are each H, OH, F, Cl, Br, I, NO$_2$, NO, SO$_2$, SO$_3^-$, amino, mono- and di-($C_1$-$C_{24}$-alkyl)-substituted amino, mono- and di-($C_5$-$C_{20}$-aryl)-substituted amino, imino, phosphono, phosphonato, phosphinato, phospho, phosphino, a branched or unbranched, saturated or unsaturated hydrocarbon radical which has from 1 to 30 carbon atoms and may have suitable substituents, where the hydrocarbon radical may have one or more heteroatoms in the chain, an aryl group or heteroaryl group which may have suitable substituents, where $R^{17}$ and/or $R^{18}$ radicals with $R^{20}$ may form a 5- or 6-membered ring which may be aromatic, alicyclic, heteroaromatic or heteroalicyclic and may have up to 4 substituents, $R^{20}$ is H, a hydrocarbon group such as a saturated or unsaturated, branched or linear alkyl group, alkenyl group, alkynyl group, aryl, alkylaryl, which may have suitable substituents, a heteroatom-containing hydrocarbon group which may have suitable substituents.

The catalyst is used preferably in an amount of from 0.1 to 100 mol %, in particular of from 1 to 30 mol %, and more preferably in an amount of from 0.1 to 10 mol %, based on the amount of the compound with the formula I.

In a further embodiment of the present invention, the dihydropyridine with the general formula III which has been specified as the hydride donor may also be used as a cocatalyst in addition to the actual catalyst of the formula IV. In this embodiment, $H_2$ is supplied to the reaction mixture and immediately again reduces the dihydropyridine oxidized to the pyridine after release of hydride, the pyridine then being available again for the hydrogenation of carbonyl compound. This procedure has the advantage that the hydride donor reaction component can only be used in small amounts and only the relatively inexpensive $H_2$ gas has to be supplied continuously. The reduction of the pyridine by $H_2$ can be catalyzed, for example, by the presence of a suitable chemical catalyst or of an enzyme. Alternatively to $H_2$, it is also possible for other reducing agents or electrochemical methods to be used.

To perform the process according to the invention, the starting substances, i.e. the compounds with the formula I, the hydride donor and any catalyst used, are dissolved or suspended in a suitable solvent which does not adversely affect the reaction. When one of the reaction components is present as a gas (for example the hydride donor), the solid or liquid components are present dissolved or suspended in a solvent, and the gaseous component is subsequently introduced.

The reaction is preferably performed at standard pressure. When one reactant is present as a gas, for example the hydride donor, the reaction can also be performed at higher pressures, in particular from 0.1 to 200 bar, preferably from 0.5 to 50 bar and more preferably from 0.5 to 5 bar.

The reaction temperature is unproblematic; the reaction can be performed over a range between −100° C. and 100° C., preferably between −90° C. and 50° C. In order to avoid the formation of by-products as far as possible, the reaction is preferably performed in inert gas atmosphere.

On completion of the reaction, the resulting reaction product can be isolated in a manner known per se. Typically, the solvent is removed and the resulting crude product is purified by processes well known to those skilled in the art, such as chromatography, distillation, sublimation, crystallization, recrystallization, extraction, etc.

EXAMPLES

1. Non-asymmetric conjugated reduction of enal 3a and 31 by means of Hantzsch ester 1, catalyzed by the dibenzylammonium salt of trifluoroacetic acid.

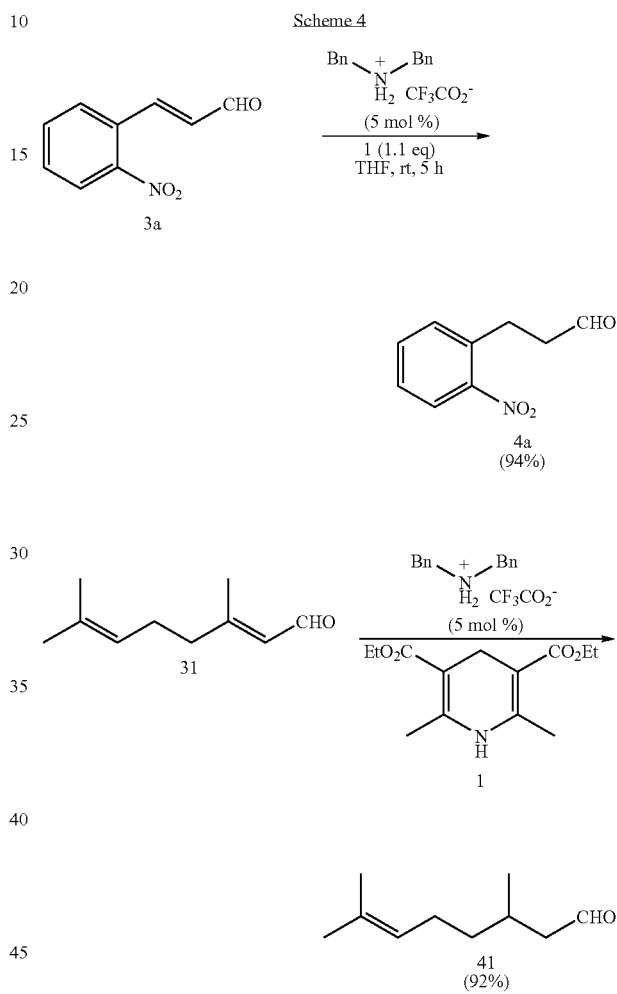

Example 1

Synthesis of the aldehyde (o-nitrophenyl)-propanal (4a)

The dihydropyridine 1 (140 mg, 0.55 mmol, 1.1 eq) was added to a solution of o-nitrocinnamaldehyde (3a, 88.6 mg, 0.5-mmol) and catalyst 2a (7.8 mg, 0.025 mmol, 5 mol %) in anhydrous THF (2 ml). The reaction mixture was stirred under argon at room temperature for 5 h.

Subsequently, the solvent was removed and the residue was chromatographed by means of silica gel (30% diethyl ether/n-hexane). 84 mg (94%) of 3-(o-nitrophenyl)-propanal (4a) were obtained as an oil.

Analogously to example 1, the compounds shown in the table below were reacted and obtained.

| Entry | Substrate | Product | Yield (%)[a] |
|---|---|---|---|
| (1) | 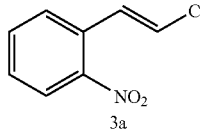 3a | 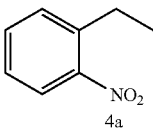 4a | 94 |
| (2) | 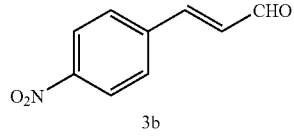 3b | 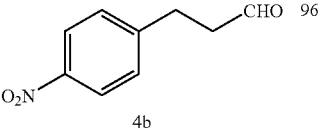 4b | 96 |
| (3) | 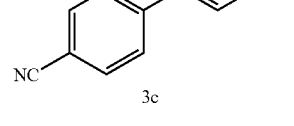 3c | 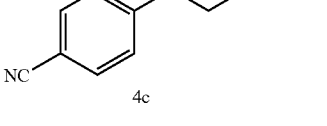 4c | 93 |
| (4) | 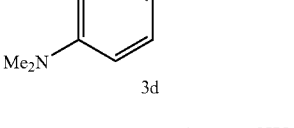 3d | 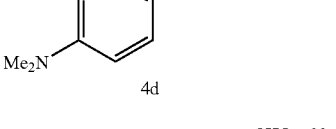 4d | 81[b] |
| (5) | 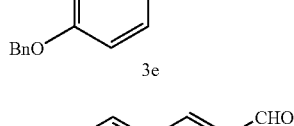 3e | 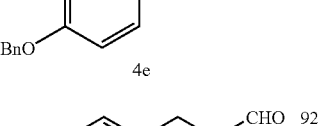 4e | 92 |
| (6) | 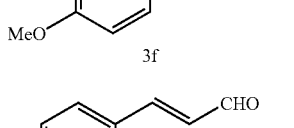 3f | 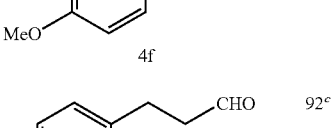 4f | 92 |
| (7) | 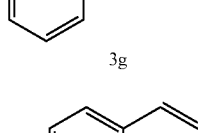 3g | 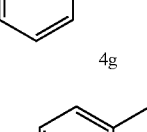 4g | 92[c] |
| (8) | 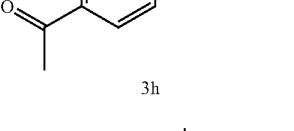 3h | 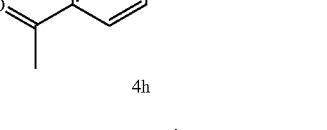 4h | 90 |
| (9) | 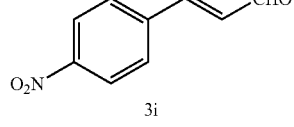 3i | 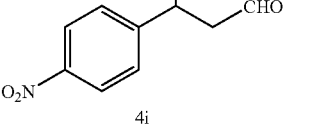 4i | 94 |

-continued (2)

R'\C(R)=CH-CHO  →[1 (1.1 eq), 2a (5 mol %), THF, rt, 5-6 h]  R'\CH(R)-CH2-CHO
   3                                                              4

| Entry | Substrate | Product | Yield (%)[a] |
|---|---|---|---|
| (10) | 3j | 4j | 90[b,a] |
| (11) | 3k | 4k | 86[b,a] |
| (12) | 3l | 4l | 92 |

2. Asymmetric conjugated reduction of enals with catalyst 5.

Example 2

Synthesis of (R)-4-(1-methyl-3-oxopropyl)benzonitrile

The dihydropyridine 6 (1.1 eq) was added to a solution of (E)- or (Z)-4-(1-methyl-3-oxopropenyl)benzonitrile (0.5 mmol) (or an E/Z mixture) and catalyst 5 (10 mol %) in anhydrous dioxane (7 ml). The reaction mixture was stirred under argon at 13° C. for 36 h. Subsequently, the solvent was removed and the residue was chromatographed by means of silica gel. The product obtained was (R)-4-(1-methyl-3-oxopropyl)benzonitrile in 90% yield and in an enantiomeric ratio of 97.5:2.5.

Various other unsaturated aldehydes were reacted in an analogous manner (scheme 6).

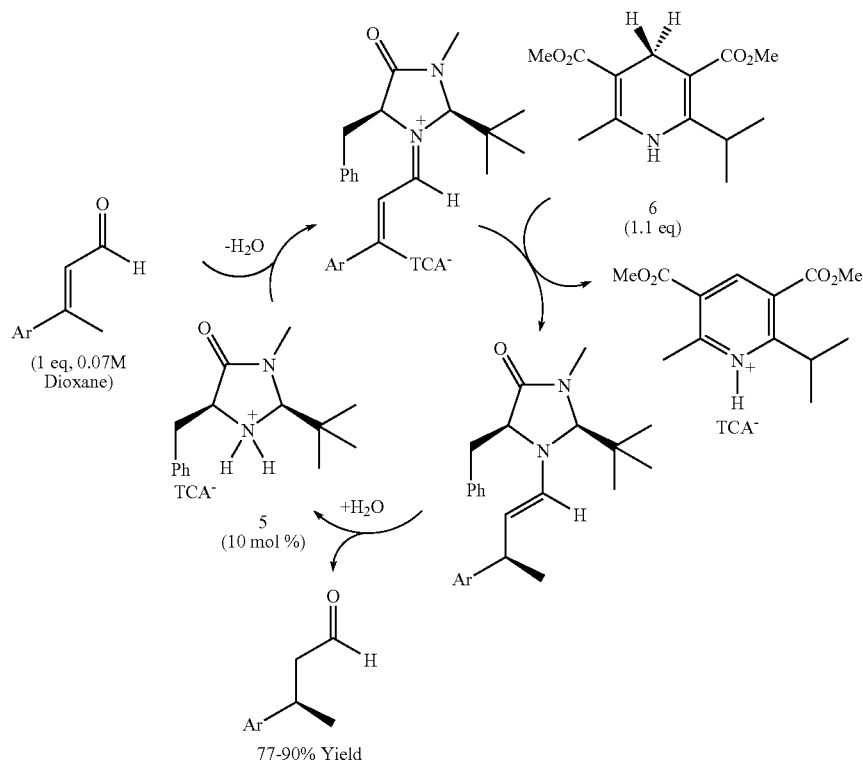

Scheme 6: Inventive use examples

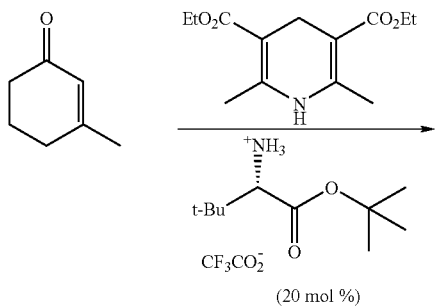

| Ar = | er |
|---|---|
| Ph | 94.5:5.5 |
| 4-NCC$_6$H$_4$ | 97.5:2.5 |
| 4-NO$_2$C$_6$H$_4$ | 96:4 |
| 4-BrC$_6$H$_4$ | 96.5:3.5 |
| 4-F$_3$CC$_6$H$_4$ | 97:3 |
| 2-Naphthyl | 95:5 |

Example 3

Hydrogenation of a Ketone

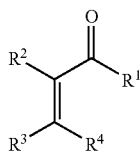

59% ee

The dihydropyridine 1 (1.1 eq) was added to a solution of 3-methylcyclohexanone (0.5 mmol) and catalyst (0.1 mmol; 20 mol %) in anhydrous 1,4-dioxane (2 ml). The reaction mixture was stirred under argon at room temperature for 4 days. Subsequently, the solvent was removed and the residue was chromatographed by means of silica gel (30% diethyl ether/n-hexane). The ketone was isolated with an ee value of 59%.

The invention claimed is:

1. A process for hydrogenating α, β-unsaturated carbonyl compounds, comprising reacting a compound of the formula I with a hydride donor in the presence of a catalyst to form a compound of the formula II, wherein the compound of the formula I has the formula:

(I)

in which $R^1$ is H, a branched or unbranched, saturated or unsaturated hydrocarbon radical which has from 1 to 30 carbon atoms and may have suitable substituents, where the hydrocarbon radical may have one or more heteroatoms in the chain, an aryl group or heteroaryl group which may have suitable substituents, $R^2$, $R^3$ and $R^4$ may be the same or different and are each selected from the group consisting of H, F, Cl, Br, I, OH, CN, NO$_2$, NO, SO$_2$, SO$_3^-$, amino, mono- and di-(C$_1$-C$_{24}$-alkyl)-substituted amino, mono- and di-(C$_5$-C$_{20}$-aryl)-substituted amino, imino, phosphono, phosphonato, phosphinato, phospho, phosphino, a branched or unbranched, saturated or unsaturated hydrocarbon radical which has from 1 to 30 carbon atoms and may have suitable substituents, where the hydrocarbon radical may have a heteroatom in the chain, an aryl group or heteroaryl group which may have suitable substituents, where in each case 2 or more of the $R^1$, $R^2$, $R^3$ and $R^4$ radicals may form a 5- or 6-membered ring or fused 5-membered and/or 6-membered rings, which may be aromatic, alicyclic, heteroaromatic or heteroalicyclic and may have up to 4 substituents, and the compound of the formula II has the formula:

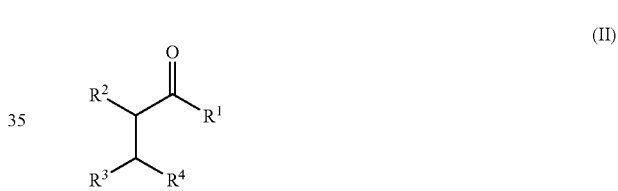

in which $R^1$, $R^2$, $R^3$ and $R^4$ are each as defined above; and where in the catalyst is selected from the group consisting of organic bases.

2. The process as claimed in claim 1, wherein the hydride donor is selected from dihydropyridines, secondary alcohols, silanes, triarylmethanes, cyclohexadienes, formaldehyde and its derivatives, formic acid and its derivatives and salts.

3. The process as claimed in claim 2, wherein the hydride donor is a dihydropyridine of the formula III

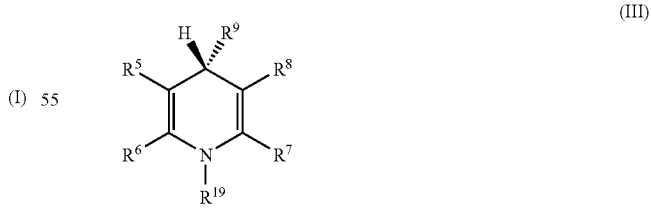

in which $R^5$, $R^6$, —$R^7$, Re and $R^9$ may be the same or different and are independently H, OH, a saturated or unsaturated, straight-chain, branched or cyclic, unsubstituted or substituted C$_1$-C$_{20}$-alkyl radical, halogen, NO$_2$, an amino group, —CO$_2$R$^{10}$, C(O)R$^4$, C—O—R$^{12}$, OR$^{13}$, where R$^{10}$ to R$^{13}$ may each be selected from H, branched or unbranched, saturated or unsaturated hydrocarbon radicals which have 1 to 30 carbon atoms and may have suitable substituents, where the hydrocarbon radicals may have one or more heteroatoms in the chain, aryl groups or heteroaryl groups, which may in turn have suitable substituents, and $R^{19}$ is H, a branched or unbranched, saturated or unsaturated hydrocarbon radical which has from 1 to 30 carbon atoms and may contain suitable substituents, where the hydrocarbon radicals may have one or more heteroatoms in the chain and suitable substituents, aryl groups or heteroaryl groups which may in turn have suitable substituents, and salts of the compounds with the formula III.

4. The process as claimed in claim 1, wherein the catalyst is selected from the group consisting of amines and acid addition salts thereof.

5. The process as claimed in claim 4, wherein the catalyst is selected from amines with the formula IV $$NHR^{14}R^{15} \qquad (IV)$$

in which $R^{14}$ is H, a saturated or unsaturated, branched or linear alkyl group, alkenyl group, alkynyl group, aryl, alkylaryl, which may have suitable substituents, or a heteroatom-containing hydrocarbon group which may have suitable substituents, and $R^{15}$ is a saturated or unsaturated, branched or linear alkyl group, alkenyl group, alkynyl group, aryl, alkylaryl, which- may have suitable substituents, a heteroatom-containing hydrocarbon group which may have suitable substituents, where $R^{14}$ and $R^{15}$ may form a fused, substituted or unsubstituted ring which has from 3 to 7 carbon atoms and may, in addition to the nitrogen atom from formula IV, also contain a further heteroatom, and their acid addition salts.

6. The process as claimed in claim 5, wherein the amine is selected from imidazolidinone and its derivatives with the formula V:

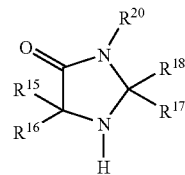

(V)

in which $R^{15}, R^{16}, R^{17}$ and $R^{18}$ may be the same or different and are each selected from the group consisting of H, OH, F, Cl, Br, I, $NO_2$, NO, $SO_2$, $SO_3^-$, amino, mono- and di-($C_1$-$C_{24}$-alkyl)-substituted amino, mono- and di-($C_5$-C20-aryl)-substituted amino, imino, phosphono, phosphonato, phosphinato, phospho, phosphino, a branched or unbranched, saturated or unsaturated hydrocarbon radical which has from 1 to 30 carbon atoms and may have suitable substituents,-where the hydrocarbon—radical may have one or more heteroatoms in the chain, an aryl group or heteroaryl group which may have suitable substituents, where $R^{17}$ and/or $R^{18}$ radicals with $R^{20}$ may form a 5- or 6-membered ring which may be aromatic, alicyclic, heteroaromatic or heteroalicyclic and may have up to 4 substituents, $R^{20}$ is H, a saturated or unsaturated, branched or linear alkyl group, alkenyl group, alkynyl group, aryl, alkylaryl, which may have suitable substituents, a heteroatom-containing hydrocarbon group which may have suitable substituents.

* * * * *